United States Patent
Xie et al.

(10) Patent No.: US 11,865,155 B2
(45) Date of Patent: *Jan. 9, 2024

(54) **PLANT EXTRACT OBTAINED FROM *MORUS* PLANT LEAVES WHICH HAS AN IC50 VALUE TO INHIBIT A-GLUCOSIDASE I AT A CONCENTRATION OF LESS THAN 90 UG/ML, COMPOSITIONS CONTAINING SAME, METHOD OF EXTRACTION AND USES THEREOF**

(71) Applicant: Botanic Century (Beijing) Co. Ltd., Beijing (CN)

(72) Inventors: Chen Xie, Beijing (CN); Yingshu Zou, Beijing (CN)

(73) Assignee: Botanic Century (Beijing) Co. Ltd.

( * ) Notice: Subject to any disclaimer, the term of this patent is extended or adjusted under 35 U.S.C. 154(b) by 42 days.

This patent is subject to a terminal disclaimer.

(21) Appl. No.: 17/367,308

(22) Filed: Jul. 2, 2021

(65) Prior Publication Data

US 2021/0330727 A1    Oct. 28, 2021

Related U.S. Application Data

(63) Continuation of application No. 16/010,402, filed on Jun. 15, 2018, now Pat. No. 11,090,349, which is a continuation of application No. 14/621,359, filed on Feb. 12, 2015, now Pat. No. 10,016,474, which is a continuation of application No. 13/496,427, filed as application No. PCT/CN2010/076988 on Sep. 16, 2010, now Pat. No. 8,980,343.

(30) Foreign Application Priority Data

Sep. 16, 2009    (CN) .................... 200910307065.X

(51) Int. Cl.
| | | |
|---|---|---|
| *A61K 36/605* | (2006.01) | |
| *A23L 33/105* | (2016.01) | |
| *A61K 8/9789* | (2017.01) | |
| *A61K 8/9794* | (2017.01) | |
| *A61Q 19/02* | (2006.01) | |

(52) U.S. Cl.
CPC .......... *A61K 36/605* (2013.01); *A23L 33/105* (2016.08); *A61K 8/9789* (2017.08); *A61K 8/9794* (2017.08); *A61Q 19/02* (2013.01); *A23V 2002/00* (2013.01)

(58) Field of Classification Search
CPC .. A61K 36/605; A61K 8/9789; A61K 8/9794; A61K 8/97; A61K 2236/39; A23L 33/105; A61Q 19/02; A23V 2002/00; A23V 2200/318; A61P 3/10; A61P 3/00; A61P 3/08; A61P 17/00; A61P 35/00; A61P 43/00

See application file for complete search history.

(56) References Cited

U.S. PATENT DOCUMENTS

| | | |
|---|---|---|
| 2001/0018090 A1 | 8/2001 | Noda et al. |
| 2003/0077339 A1 | 4/2003 | Yoon et al. |
| 2003/0161903 A1 | 8/2003 | Konishi et al. |
| 2004/0033276 A1 | 2/2004 | Ra et al. |
| 2004/0042984 A1 | 3/2004 | Park et al. |
| 2006/0024396 A1 | 2/2006 | Konishi et al. |
| 2006/0172020 A1 | 8/2006 | Djang |
| 2007/0009615 A1 | 1/2007 | Zhong |
| 2007/0036874 A1 | 2/2007 | Zhong |
| 2007/0248619 A1 | 10/2007 | Chang Cabezas |
| 2008/0241292 A1 | 10/2008 | Heuer et al. |
| 2009/0214682 A1 | 8/2009 | Heuer et al. |
| 2010/0202980 A1 | 8/2010 | Fogel |
| 2010/0247686 A1 | 9/2010 | Zhong |
| 2011/0052732 A1 | 3/2011 | Ueda |
| 2011/0130352 A1 | 6/2011 | Liu |
| 2012/0087997 A1 | 4/2012 | Shmulewitz et al. |

FOREIGN PATENT DOCUMENTS

| | | |
|---|---|---|
| CN | 101007017 A | 8/2007 |
| CN | 101224240 A | 7/2008 |
| EP | 2255822 A1 | 12/2010 |
| JP | 2004105157 A | 4/2004 |
| JP | 2004194635 A | 7/2004 |
| JP | 2005343808 A | 12/2005 |
| JP | 2007060908 A | 3/2007 |
| KR | 20080091632 A | 10/2008 |
| WO | WO-2005009351 A2 | 2/2005 |
| WO | WO-2006119038 A1 | 11/2006 |
| WO | WO-2008025249 A1 | 3/2008 |

OTHER PUBLICATIONS

Kimura T. et al. Food Grade Mulberry Powder Enriched with 1-Deoxynojirimycin . . . J Agricultural and Food Chem 55:5869-5874, 2007. (Year: 2007).*

Asano, N. et al. Polyhydroxylated Alkaloids Isolated from Mulberry Trees and Silkworms. J Agricultural and Food Chem 49:4208-4213, 2001. (Year: 2001).*

Liu, Yinhua etc., "Inhibition of extract from mulberry leaves on tyrosinase activity, Chinese Journal of Clinical Rehabilitation", Jan. 21, 2005, vol. 9, No. 3, p. 164-165.

(Continued)

*Primary Examiner* — Aaron J Kosar

(74) *Attorney, Agent, or Firm* — Fishman Stewart PLLC

(57) ABSTRACT

An extract from leaves of mulberry is disclosed. The extract has an IC50 value sufficient to inhibit a-glucosidase I. The extract may comprise 5-40% (w/w) total imino sugars and 20-70% (w/w) total amino acids. The extract may reduce the production of melanin for the treatment of such ailments or diseases caused by pigmentation as freckle, chloasma, striae gravidarum, sensile plaque and melanoma. The extract may also control blood glucose level.

20 Claims, 8 Drawing Sheets

(56) References Cited

OTHER PUBLICATIONS

Butt, M.S. et al.: "*Morus alba* L. nature's functional tonic", Trends in Food Science & Technology, Elsevier Science Publishers, GB, vol. 19, No. 10, Oct. 1, 2008, pp. 505-512.
English Abstract for JP 2014105157.
English Abstract for JP 2005343808.
English Abstract for KR 20080091632.
English Abstract for JP 2004194635.

* cited by examiner

PLANT EXTRACT OBTAINED FROM *MORUS* PLANT LEAVES WHICH HAS AN IC50 VALUE TO INHIBIT A-GLUCOSIDASE I AT A CONCENTRATION OF LESS THAN 90 UG/ML, COMPOSITIONS CONTAINING SAME, METHOD OF EXTRACTION AND USES THEREOF

CROSS-REFERENCE TO RELATED APPLICATIONS

This application is a continuation application of U.S. patent application Ser. No. 16/010,402, filed Jun. 15, 2018, which is a continuation of U.S. patent application Ser. No. 14/621,359, filed Feb. 12, 2015, which is a continuation of U.S. application Ser. No. 13/496,427, filed Jun. 4, 2012 (U.S. Pat. No. 8,980,343, issued Mar. 17, 2015), which claims priority to Chinese Patent Application No. 200913007065.X, filed on Sep. 16, 2009 and PCT/CN2010/076988, filed on Sep. 16, 2010. The content of all of these applications is hereby incorporated by reference in their entirety.

TECHNICAL FIELD

The present disclosure relates to a plant extract, compositions containing same, a method of extraction and to the use of said extract.

Mulberry leaves have a long history of medicinal use in Asian countries, in particular China. In recent years, phytochemists have isolated a number of imino sugar constituents from mulberry leaves, such as 1-deoxynojirimycin (DNJ), fagomine, and N-methyl-DNJ. The chemical structures of the imino sugars are similar to that of monosaccharides, being mostly polyhydroxyl heterocyclics with a 5 to 6-membered ring. The key difference between the two lies in the hetero atoms of the heterocycle. The former contains nitrogen atoms (N) while the latter oxygen (O).

It has been shown that the imino sugar constituents from mulberry leaves exhibit certain inhibitory activity on α-glucosidase I and II, among which DNJ showed the strongest activity. Further pharmacological experiments revealed that DNJ acted on melanocyte inhibiting the maturing process of TYR, which resulted in the reduction of melanin production. (Genji Imokawa, Analysis of Carbohydrate Properties Essential for Melanogenesis in TYRs of Cultured Malignant Melanoma Cells by Differential Carbohydrate Processing Inhibition. *The Journal of Investigative dermatology*, 1990, 95(1):39-49; Ju Young Park, hyunjung Choi, Jae Sung hwang, Junoh Kim, Ih-Seop Chang, Enhanced depigmenting effects of N-glycosylation inhibitors delivered by pH-sensitive liposomes into HM3KO melanoma cells, *Journal of Cosmetic Science*, 2008, 59:139-150.)

The inventors carried out sets of enzyme experiments and found that the total imino sugar extract (as measured by the content of 1 deoxynojirimycin (DNJ), N-methyl-DNJ, and fagomine) from mulberry leaves as described in the extracts of the present disclosure possessed more potent inhibitory activity on α-glucosidase I and II than the pure chemical DNJ. This discovery makes it possible to use such mulberry extracts to achieve inhibition of α-glucosidase I and II with lower concentrations of DNJ, thereby reducing the likelihood of possible adverse drug reaction (ADR) and making the finished product safer to use. In addition, since the cost of producing the mulberry extract, as described in the present disclosure, is much lower than that of obtaining the pure chemical DNJ, the cost of treating hyper-pigmentation related ailments could be greatly reduced.

Thus, cosmetics and pharmaceuticals made from such extracts have huge advantages in efficacy, safety and cost over those containing pure chemicals such as DNJ, the structure of which is given below.

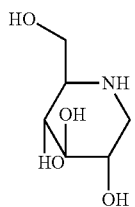

Structure of 1 -deoxyjirimycin (DNJ)

In the past, there have been a number of researchers in China or abroad who have tried to commercialise mulberry extracts in the beauty product market for whitening and spot-reduction. However, by comparison, the present extract has quite different characteristics and offers a number of advantages.

Chinese patent ZL99123894X discloses a composition of plant extracts for the treatment of skin pigmentation, which is composed of a combination of three main ingredients, namely an extract from plants of the genus *Morus*, an extract from plants of the genus *Scutellaria* and derivatives of salicylic acid. The *Morus* extract of that disclosure was obtained from mulberry root, which contained mainly kuwanone and there were no clear specification of the extract.

U.S. patent application No. 347,884 discloses the use of an extract from the branches of mulberry tree for the same cosmetic purposes, with the active constituents in the extracts being oxyresvertrol and mulberroside. Compared with these two disclosures, the present disclosure has the following advantages and features:

1. Raw material advantage. The raw material, mulberry leaves, used in present disclosure, is easier to regenerate, and offers a more sustainable resource than roots and branches. It also offers a relatively lower cost than the two disclosures mentioned above.
2. Different mechanisms of action. In the two disclosures mentioned above, the activity was achieved through competitive inhibition on TYR. In the present disclosure, the mechanism of action is to reduce the production of melanin through inhibiting α-glucosidase, resulting in less mature (and less/inactive) TYR.
3. Different active principles. In the above mentioned patents, the active principles were either flavonoids, e.g. kuwanones, or diphenyl ethenoids, e.g. oxyresveratol and mulberrosides. In contrast the active principles of the present disclosure are imino sugars, and different preparation methods are employed to isolate an extract rich in these imino sugars.
4. Unique preparation process. The process is designed to ensure optimum extraction of the active ingredients and purification which to improve e.g. the physical properties of the extract, making it more suitable to be used in, for example, cosmetic products.

Melanin is the most important factor in determining the colour of human skin. It is biosynthesized in the melanosome of melanocytes at the base layer of the epidermis. Under normal physiological condition, melanin protects the skin from UV light injury. When melanin synthesis metabolism is disturbed by external factors, hormone disorders, senile processes, etc., the melanin at the epidermis base layer will increase and the colour of the skin will darken. This in turn will result in pigmentation ailments or diseases such as freckle, chloasma, striae of pregnancy, senile plaque and melanoma. Besides, there are a great number of beauty-conscious people who are longing for whiter skin and thus there is a demand for skin lightening, whitening and spot reducing agents and cosmetics.

In brief, the biosynthesis of melanin includes the following steps genesis by Kojic Acid in Rat Two-Stage Models after Initiation with N-bis(2-hydroxypropyl)nitrosamine or N-diethylnitrosamine. *Toxicological Sciences* 2004 81 (1):43-49).

Arbutin is considered as a whitening and spot-reducing beauty product with very little side effects but it is highly light-sensitive and as a result, large amounts of sun protection agents are required to be added to the finished product, which increases the burden to the skin and thus accelerates its senile process.

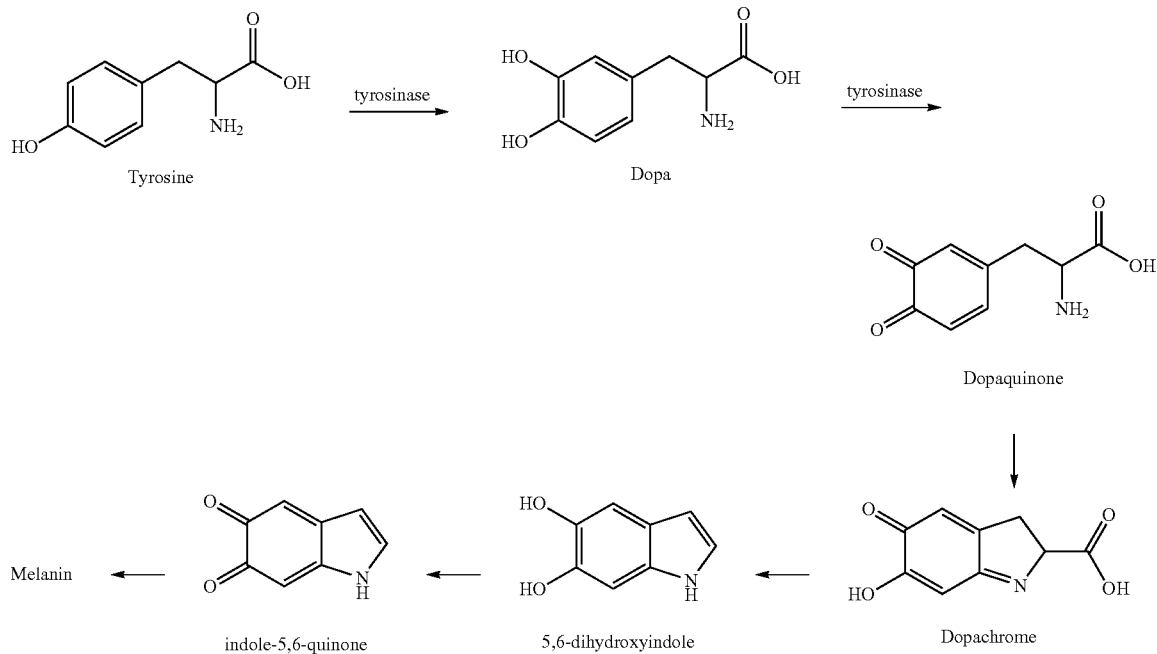

Tyrosinase (TYR), a type of glycoprotein containing ionic copper, and is the key enzyme for the biosynthesis of melanin. It catalyses the reaction to transform tyrosine to dopa and dopaquinone. TYR is considered an important target for reducing pigmentation and is used frequently in the research area for products with the function of whitening skin and reducing spots.

Currently the main way of targeting TYR is to inhibit its formation and activity to reduce the production of melanin. Current products containing TYR inhibitors include 1,4-dihydroxybenzene (hydroquinone) and its derivatives, kojic acid and its derivatives, and arbutin.

While 1,4-dihydroxybenzne and its derivatives are able to inhibit 100% activity of TYR, they also stimulate melanocytes and show cytotoxicity. Prolonged use coupled with exposure to light could cause exogenous pigment spots. They are therefore banned in skincare products.

Kojic acid is very stable and has good effects in reducing pigment spots through chelating copper ions to lower the activity of TYR. However, long term use of kojic acid could cause cytotoxicity resulting in skin diseases. Japanese researchers demonstrated that kojic acid could cause liver cancer (Tamotsu Takizawa, Toshio Imai, Jun-ichi Onose, Makoto Ueda, Toru Tamura, Kunitoshi Mitsumori, Keisuke Izumi and Masao Hirose. Enhancement of Hepatocarcino- The above shortcomings restrict the application of existing products in the market of beauty products for whitening skin and reducing spots.

TYR is a protein with a sugar chain (glycoprotein). Modern research in biochemistry has revealed that in the process of its production (and maturity) the original sugar chain must undergo a series of modifications in order to transform the newly produced TYR into mature TYR which has the normal biological functions. α-Glucosidase I and II are the key enzymes in this process. α-Glucosidase I is mainly responsible for "cleaving" the glucose moiety with α-1,2 linkage at the far end of the sugar chain while α-Glucosidase II will, in two steps, cleave the remaining two glucose moieties, linked by an α-1,3 connection. (Mehta A, Zitzmann N, Rudd P M, Block T M, Dwek R A. α-Glucosidase inhibitors as potential broad based anti-viral agents, *FEBS Letters*, 1998, 430(1):17-22).

It is believed that when α-glucosidase I and II are inhibited, the modification of the sugar chain of the glycoprotein is retarded resulting in no production of mature TYR. With "immature TYR" the production of melanin is consequently reduced in proportion. (Hiroyuki Takahashi, Peter G. Parsons, Rapid and reversible inhibition of TYR activity by glucosidase inhibitors in human melanoma cells, *The Journal of Investigative dermatology*, 1992, 98(4):481-487.)

Therefore, it would be a highly feasible approach to reduce the production of melanin and in turn the skin pigmentation by inhibiting α-glucosidase I and II to minimize the formation of mature TYR, as illustrated in FIG. 4 which shows the proposed mechanism of action for inhibition of melanin synthesis. Essential modification of tyrosinase, catalysed by α-glucosidase, is inhibited by the *Morus* extract resulting in inactive tyrosinase formation

BRIEF SUMMARY OF THE DISCLOSURE

In accordance with the present disclosure, there is provided a plant extract, obtained from *Morus* plant leaves, which has an IC so value to inhibit α-glucosidase I at a concentration of less than 90 μg/ml.

Preferably the plant has an IC so value to inhibit α-glucosidase I at a concentration of less than 70 μg/ml and more preferably from 5-60 μg/ml and more preferably still 5-40 μg/ml.

The IC so can be determined as set out in Experiment 1.

The improvement in the extracts activity over pure isolated DNJ is considered to be due to the activity of the other imino sugars present in the extract. Preferably the extract comprises 5-40% (w/w) total imino sugars as measured by quantitative HPLC and/or LC-MS (liquid chromatography/mass spectrometry). The measured imino sugars include 1 deoxynojirimycin (DNJ), N-methyl-DNJ, and fagomine.

More preferably the extract will comprise 8-30% (w/w) total imino sugars, more preferably still 15-20% (w/w) total imino sugars.

By accurately controlling the content of the characteristic chemical constituents, it becomes possible to effectively control the quality of the product thus providing certain assurance as to the cosmetic or therapeutic effect of the product.

Most preferably the extract will further comprise the imino sugars 1,4-dideoxy-1,4-imino-D-arabinitol (DAB), 2-O-α-D-galactopyranosyl-DNJ (GAL-DNJ) and calystegin B.

The presence of DAB, which is a glycogen phosphorylase inhibitor, may be of significance in the extracts use in controlling sugar metabolism which application constitutes a further aspect of the disclosure.

In addition to the imino sugars the extract preferably comprises 20-70% (w/w) total amino acids.

More preferably the extract contains from 30-60% (w/w) total amino acids, more preferably still 40-50% (w/w) total amino acids.

The amino acids present in the extract include 8 essential amino acids which human body is incapable of producing and include arginine, leucine, lysine and phenylanaline which promote the secretion of insulin. As it is well known, amino acids are essential for maintaining moisture and elasticity of the skin. Amino acid deficiency will weaken the skin metabolism and accelerate the skin senile process. (Marty J. P., NMF and cosmetology of cutaneous hydration. *Annales de Dermatologie et de Vénéréologie*, 2002, 129(1 Pt 2):131 -136.). The extract of the present disclosure will thus also function to help maintain skin health.

The extract of the disclosure is obtained from Mulberry leaves of the family Moraceae, genus *Morus* and is selected from

| | | |
|---|---|---|
| a. | *Morus alba* L. | |
| b. | *Morus alba* var. *multicaulis* L. | |
| c. | *Morus nigra* and | |
| d. | *Morus australis* Poir. | |

The inventors of the present disclosure carried out chemical analysis of the chemical constituents of the leaves of common *Morus* plants and found that the leaves of the above-mentioned species all contained relatively higher imino sugar content than other species and the leaves of *M. alba* had the highest content of imino sugars.

More preferably the imino sugar content is standardised with reference to DNJ which is present in an amount of from 1-20% (w/w) of (DNJ) calculated on the basis of the total weight of the extract, more preferably 2-10% (w/w) of (DNJ) calculated on the basis of the total weight of the extract and, depending on the intended use, either 4-6% (w/w) of (DNJ) calculated on the basis of the total weight of the extract or 1-3% (w/w) of (DNJ) calculated on the basis of the total weight of the extract. DNJ is also the predominant (highest yielding) imino sugar present. The extract of the disclosure differs from current Mulberry extracts in a number of ways including:

its colour—it is pale yellow
its solubility—it is easily soluble in water,
its pH—it has a pH value of between 5.5-6.5 in a 1% water solution, and
its UV spectrum—it shows a maximum absorption at 218 nm and 263 nm.

The extract may be produced using a novel extraction and purification process comprising three basic steps which process constitutes a further aspect of the disclosure In accordance with a second aspect of the present disclosure there is provided a method for producing an extract, from *Morus* plant leaves, which has an IC so value to inhibit α-glucosidase I at a concentration of less than 90 μg/ml comprising the steps of:

a. Conducting a water or alcoholic extraction step from leaf material;
b. Conducting a column chromatography purification step using a strong acidic cation exchange resin, washing with water, and eluting with an ammonia solution, collecting the eluent, and removing the ammonia therefrom;
c. Subjecting the eluent to column chromatography using a macroporous absorption resin, collecting the solution; and
d. Concentrating and drying the extract.

Preferably the plant leaves were oven dried and made into coarse powder and a. the extraction step is conducted with 5-18 folds of 0-40% low molecular weight alcohol per the quantity of the *Morus* plant leaves (w/w), and repeated up to 5 times,
b. the column is washed with 1-2 folds of water of the column volume and the wash discarded, the column is eluted with 2-8 folds of 0.2-1.0N ammonia water solution of the column volume, at an elution rate of 1-3 folds of the volume of the column per hour, and the eluent collected with a pH value of between 9.0 and 11.0,
c. the column is eluted with a volume ratio between the solution and column of between 20:1 to 5:1 , and
d. the dried extract is pulverized to pass through a mesh 80 sieve.

Fuller details of the extraction process to obtain the extract of the disclosure are set out below:

Extraction (Step 1): The plant leaves were oven dried and made into a coarse powder. Extract the powder with 5-18 folds of the quantity of the raw material (w/w) of 0-40% low molecular weight alcohol for 1-5 times, preferably with 10-13 folds of the quantity of the raw material (w/w) of 20-30% low molecular weight alcohol and more preferably with 11 folds of the quantity of the raw material (w/w) of 25% low molecular weight alcohol, to obtain the liquid extract.

Purification 1 (Step 2): Column chromatography using a cationic exchange resin: After filtration of the liquid extract obtained in step (1), the solution is put through a column filled with a strong acidic cationic resin. Elute the column with 1-2 folds, preferably 1.5 folds, of the column volume of water, and discard the eluent. Further elute the column with 2-8 folds of the column volume of 0.2-1 .0N ammonia water solution, preferably 5 folds, 0.7N ammonia water solution, with an elution rate of 1-3 folds of the volume of the column per hour, preferably 1.5 folds per hour. Collect the eluent with pH values of between 9.0 and 11.0.

Purification (Step 3): Column chromatography using macroporous absorption resin: Remove ammonia from the eluent in step (2) and adjust to pH 7. Put the solution through the column filled with a macroporous absorption resin. The volume ratio between the solution and column should be 20:1 to 5:1 , preferably 15:1 to 10:1 and more preferably 13:1 . Concentrate the collected fluid run through the column and dry the concentrate, which is then pulverized to pass through a mesh 80 sieve to obtain the extract of the present disclosure.

Based on the aforesaid extraction method at step (1), the said low molecular weight alcohol should be straight chain alkyl alcohol with no more than 4 carbon atoms, preferably, methanol or ethanol. The said extraction is reflux extracted for 1-3 hours, preferably 1 -2 hours and more preferably 2 hours.

After filtration of the liquid extract obtained in step (1), further measures can be adapted to remove more impurities, improve the bioactivity of the extract and decolourize the extract. Those measures include alcohol precipitation, flocculent precipitation, and others appropriate for the removal of proteins, tannins and polysaccharides. The precipitates can be removed by either centrifuge or filtration. The preferred purification method herein is alcohol precipitation and centrifuging: Concentrate the infusion to ¼ of the original volume, add 1-3 folds of 95% ethanol, stir for half an hour and leave it for 8-12 hours, centrifuging at 12000 r/min for 15 min. Keep the supernatant for further purification.

Based on the extraction method described herein, the total volume of the liquid extract at step (2) should be 2-20 folds of the cationic exchange resin column, preferably 10-15 folds and more preferably 13 folds.

Under these conditions the active constituents can be effectively absorbed by the cationic exchange resin which helps increase the content of the active chemicals.

The strong acidic cationic resin used herein can be selected from the following types: 001X7 (#732), Amberlite IR-120, Dowex-50, Lewatit-100, Zrolit 225 or Diaion SK-1 , etc, with 001 X7 (732) as the most preferred due to its better absorption property to concentrate the active constituents and lower cost.

During the elution of the cation exchange resin column using ammonia water, the pH value of the eluent increased gradually. Biological and chemical analysis of the eluent revealed that the content of fractions with pH 9-1 1 showed the highest activity and hence only those fractions with pH 9-11 were collected.

Based on the extraction method described herein, the flow rate at step (3) should be 1-4 folds, preferably 2 folds, of the volume of the column per hour. This ensures the maximum absorption of coloured impurities by the macroporous resin ensuring good decolourisation.

Four types of macroporous resins can be selected for the aforesaid column chromatography: AB-8, HP20, S-8 and YWDO3F4. After process comparison and validation, it was found that resin S-8 produced the best decolourization result and thus Type S-8 resin is the preferred macroporous resin material.

The mulberry leaf extract obtained according to the above process has a maximum absorption peak at 218.3 nm under UV scan and is pale yellow in colour, which is distinguishable from that of other mulberry leaf extracts currently available on the market. Most mulberry leaf extracts used in beauty products on the market have deeper colour, i.e. either yellow or brownish yellow, resulting in coloured finished products, which is not considered as an ideal appearance.

The extract described in the present disclosure is easily soluble in water and this provides for better diffusion and absorption of the active ingredients on the targeted area. The mulberry extracts currently used in beauty whitening products contained flavonoids (e.g. kuwanones) and diphenyl ethenoids (e.g. oxyresveratol and mulberrosides) and as a result they have relatively poor water solubility with average diffusibility, which in practice requires the use of low molecular weight alcohol to improve solubility, thus increasing the burden on the skin.

The extract described in the present disclosure has a pH value of 5.5-6.5 in a 1% water solution. This slightly acidic pH is close to the pH of the sebum film on the surface of the skin which is 4.5-6.6. When said extract is made into skincare products, the irritation to the skin caused by the active constituents is therefore reduced.

The extract of the present disclosure may be formulated for use as a pharmaceutical or cosmetic for use as a skin lightening agent or to reduce skin hyperpigmentation or as a pharmaceutical, nutraceutical or food or drink ingredient to control blood glucose levels. Thus, it may be used to, for example, treat type 2 diabetes or to lower the glycaemic index of a food or drink.

In accordance with a third aspect of the present disclosures there is provided a plant extract according to the first aspect of the disclosure or the product of the process according to a second aspect of the disclosure for use as a cosmetic or medicament to treat conditions caused by pigmentation.

Preferably the cosmetic or therapeutic application is to reduce the production of melanin, including the treatment of ailments or disease caused by hyperpigmentation including: freckle, chloasma, striae of pregnancy, senile plaque and melanoma.

A pharmacological experiment using the mulberry leaf extract of the present disclosure revealed that the said extract effectively inhibited the activity of α-glucosidase with higher potency than a quantitatively equivalent sample of pure DNJ. It required only half the concentration of DNJ for the extract to achieve the same effect to that of pure DNJ. When tested in cell lines, the said extract showed significant inhibition effect against melanin formation in melanoma cell lines A375 and B16 and the potency was higher than that of frequently used ingredients in the marketed beauty whitening products, such as arbutin and magnesium L-ascorbyl-2-phosphate. The mechanisms of action of the mulberry leaves extract of the present disclosure differ from that of arbutin and magnesium L-ascorbyl-2-phosphate. The latter two directly and competitively inhibit the activity of TYR, while the said mulberry leaf extract mainly inhibits the formation of the mature, active TYR. The advantage of said mulberry leaf extract includes higher potency and longer action. Because of the different mechanisms of action, said extract of the present disclosure can be used alone or together with the above mentioned TYR inhibitors. A human clinical study confirms this in vitro data and after 28 days of topical application of a 0.2% or a 0.5% mulberry leaf extract cream formulation there was a significant reduction in skin pigmentation (P<0.001) and a significant lightening of the skin (P<0.001)

In accordance with a forth aspect of the present disclosures there is provided a plant extract according to the first aspect of the disclosure or the product of the process according to a second aspect of the disclosure for use in controlling blood glucose level.

Preferably the extract for use in controlling blood glucose further comprises a glycogen phosphorylase inhibitor.

In the animal experiment using Wistar rat model, and the human clinical study, the mulberry leaves extract of the present disclosure demonstrated significant blood glucose lowering effect.

The extract of the disclosure is particularly good since it benefits from a combination of actives. Thus, the imino sugar constituents, such as DNJ, inhibit α-glucosidase in the gut, resulting in the reduction of absorption of saccharides (Asano N., Glycosidase inhibitors: update and perspectives on practical use. Glycobiology, 2003, 13(10): 93R -104R.). Another of the imino sugars 1,4-dideoxy-1,4-imino-D-arabinitol (D-AB1), was found to have strong inhibitory activity against liver glycogen phosphorylase and also to inhibit in vivo the decomposition of liver glycogen. As a result it is anti-hyperglycaemic. Furthermore, the presence of the amino acids such as arginine, leucine, lysine and phenylalanine, have the function of promoting the secretion of insulin.

Thus, the extracts described in the present disclosure can be used to control after-meal blood glucose levels and adjust blood glucose balance.

Such extracts can be formulated for use as a medicament or health product (such as a food additive or supplement) for the control of blood glucose.

To provide for the third aspect the extract may be formulated as a cosmetic or medicament comprising excipients and optionally one or more alternative actives.

For use as a skin lightening agents other actives may be selected from, for example, vitamin C and its derivatives, such as vitamin-magnesium phosphatidate, kojic acid, arbutin, diacetylboldin, azelaic acid, octadecenedioic acid, undecylenoylphenylalanine (DEP-11), licorice extract, Aloe extract, watercress (*Nastutium officinale*) extract, *Ascophyllum* extract (*Ascophyllum nodosum*), hops (*Humulus lupulus*) extract, glutathione, ecdysone and/or ellagic acid.

A preferred cosmetic or medicament comprises the extract of the disclosure together with the vitamin C derivative, magnesium L-ascorbyl-2-phosphate (VC-PMG).

Preferably, in a combination product the extract is present in the ratio of 10:1 to 1:1 extract to other skin lightening agent, more preferably 5:1.

When manufacturing cosmetics or drugs for skin diseases using the mulberry leaf extract of the present disclosure or a composition also containing other ingredients, all the common base materials acceptable in pharmaceutics can be used, which include water soluble base materials such as glycerin, polyethylene glycol, cellulose derivatives, etc and liposoluble base materials such as fat, lipids, Hydrocarbons, etc. The following excipients are also commonly used, and include preservatives, such as nipagins, chlorobutanol and sorbic acids; antioxydants such as sodium sulphite, sodium bisulfate, BHT, etc; thickeners, such as stearic acid, bees wax, paraffin, laury alcohol, carboxmethyl cellulose (CMC), etc; emulsifiers such as triethanolamin, glycerol monostearate, Tweens, etc; sunscreen agents such as octyl methoxycinnamate, benzophenone-3, etc; humectants (moisturizer) such as glycerin, propylene glycol, sorbitol, etc; deodorants, fragrance and colouring agents, etc. The quantities of the above mentioned excipients will be known to the skilled person.

When the said extract is used in cosmetic products for reducing the production of melanin, the recommended quantity in the finished product should be 0.05-2%, preferably 0.1-1% and more preferably 0.2-0.5% (wt/wt).

To provide for the fourth aspect the extract may be formulated in a pharmaceutical or nutraceutical, added to a food or drink or provided as a supplement for adding thereto in an effective amount.

In a food or drink it functions to lower the glycaemic index. In such cases a dose of from 50-600 mg per serving (depending on size) may be used.

When manufacturing an oral drugs for the control of blood glucose level the mulberry leaf extract of the present disclosure may be formulated with common excipients for oral drugs such as, disintegrating agents (e.g., Dry starch, Carboxymethyl starch sodium, L-HPC, Cross linked-PVP, etc); lubricants (e.g., Magnesium stearate, Talc powder, Sodium benzoate, Polyethylene glycol 4000, etc) and adhesives (e.g., CMC).

When the said extract is used for controlling blood glucose level, based on the concentrations of the active constituents in the extract, the recommended dose is 25-600 mg each time, 3 times daily; preferably 100-300 mg each time, 3 times daily; more preferably 50-150 mg each time, 3 times daily.

Conventionally, the following forms of products can be made for cosmetics or drugs for skin diseases. These forms include solutions containing water, water-alcohol or oil, gel/colloids containing water or oil, micro-emulsions, dilute or thick emulsions, loose or dense powders, dispersions with oil in water phase formed with the aid of micro particles such as polymer particles and capsules, and best of all, ion or non-ion lipid vesicles.

When manufacturing cosmetics or drugs for skin diseases using the mulberry leaf extract or a composition they may appear in the following "dosage forms" with relative fluidity: cream, ointment, lotion, milky liquid, emulsion fluid, mucilage, paste, foam, aerosol, and anhydrous solid preparation (e.g. stick-shaped).

When manufacturing the oral drugs using the mulberry leaves extract of the present disclosure to control blood glucose level, they can be made into commonly used oral dosage forms such as tablets, capsules and powders.

BRIEF DESCRIPTION OF THE DRAWINGS

Embodiments of the invention are further described hereinafter with reference to the accompanying drawings, in which.

DETAILED DESCRIPTION

The HPLC of FIG. 1 was obtained using a set up as follows:
Instrument: Waters (USA) HPLC apparatus w600-2420-717, Empower data process system.
Column: Old Shodex Asahipak NH2P-50E (250×4.65 μηη) column used in reverse.
Reagents: Acetonitrile-water containing 6.5 nmol ammonium acetate.
Column: temperature 40° C.
Flow rate: 1.0 ml/min
Detector: W2420 ELSD
Gain: 100; Drift tube temperature 50° C.; Sprayer heating level 60%
Mobile phase: Acetonitrile : Water (containing 6.5nmol ammonium acetate) (84 16)

Figure 2:
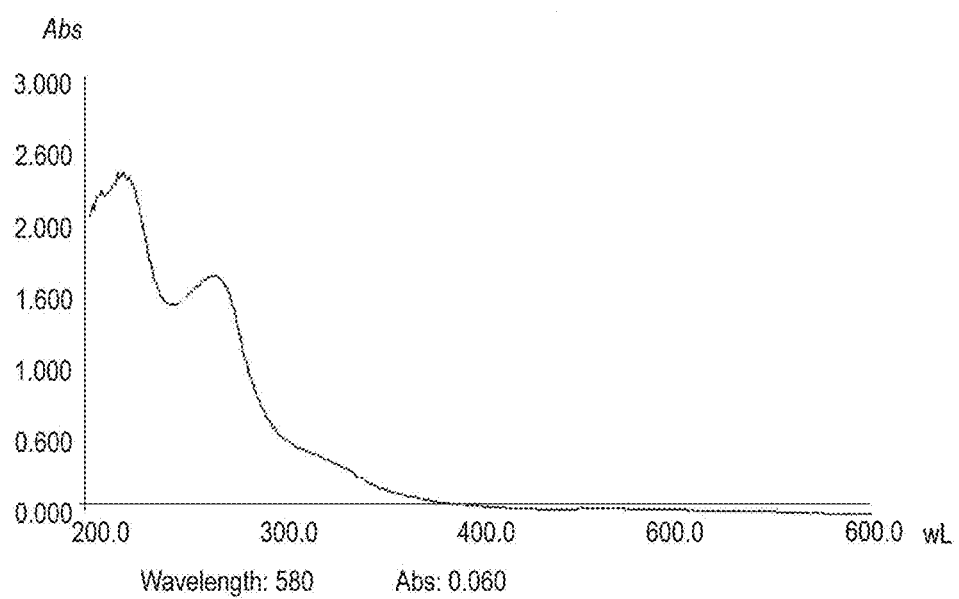
FIG. 2 is the UV spectrum of the plant extract of Example 1.
Figure 3:
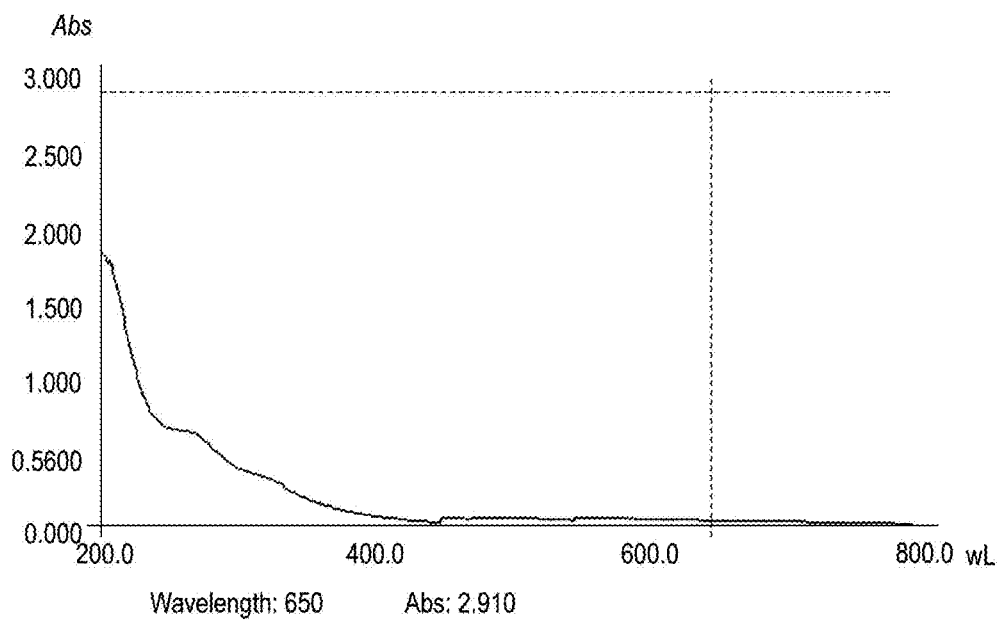
FIG. 3 is a UV spectrum of a prior art extract.
Figure 4:
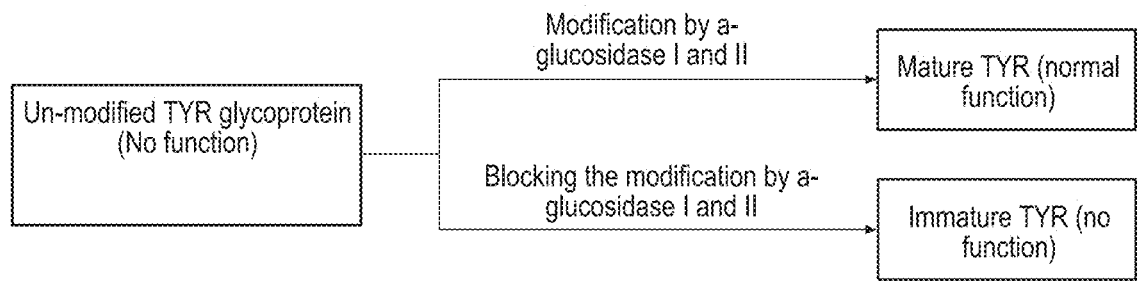
FIG. 4 is a schematic illustrating the mechanism of action behind the pigmentation reduction.

The UV spectrum of FIG. 2 and FIG. 3 was obtained using
Instrument: UNICO UV-2100 Spectrophotometer
Scan wavelength: 200-600 nm
Sample concentration: 1 mg/ml The plant extract of the disclosure may be obtained by methodology as described with reference to Examples 1 to 5 and using different mulberry leaves as illustrated with reference to Examples 6 to 9.

The plant extract of the disclosure may be obtained by methodology as described with reference to Examples 1 to 5 and using different mulberry leaves as illustrated with reference to Examples 6 to 9.

The resulting plant extract can be formulated for use as a cosmetic or medicament or as a food or drink supplement or additive as illustrated with reference to Examples 10 to 16.

The different activities of the extract are further illustrated by way of Experiments 1 to 8.

EXAMPLE 1

Pulverize 100 kg of dry mulberry leaves of the species Morus alba and extract under reflux 3 times (1 hour each time) with 12 folds of 30% ethanol (compared to the weight of the raw material). Condense the extract to a given volume and pass it through a column filled with a strong acidic cationic resin, such as 001×7. The volume of the column was 1/14 of the extracted liquid. The column was washed with water (1.5 folds of the column volume) and the component of interest (imino sugars) released from the column using 0.7 N ammonia water (5 folds of the column volume), at a flow rate of 1.5 folds of the column volume per hour. The ammonia water eluent with a pH of 9-11 was collected. The eluent was condensed to a given volume, the ammonium removed and the pH adjusted to pH 7. The eluent was then passed through a column filled with a macroporous resin, such as S-8. The volume of the column was 1/10 of the eluent liquid and the flow rate 2 folds of the column volume per hour. The collected fluid was then dried under vacuum and the dried product pulverized to pass through an 80 mesh sieve. 1.4 kg of a pale yellow powder was obtained, which contained 5.8% DNJ, 21% total imino sugars and 48% total amino acids.

Figure 1:
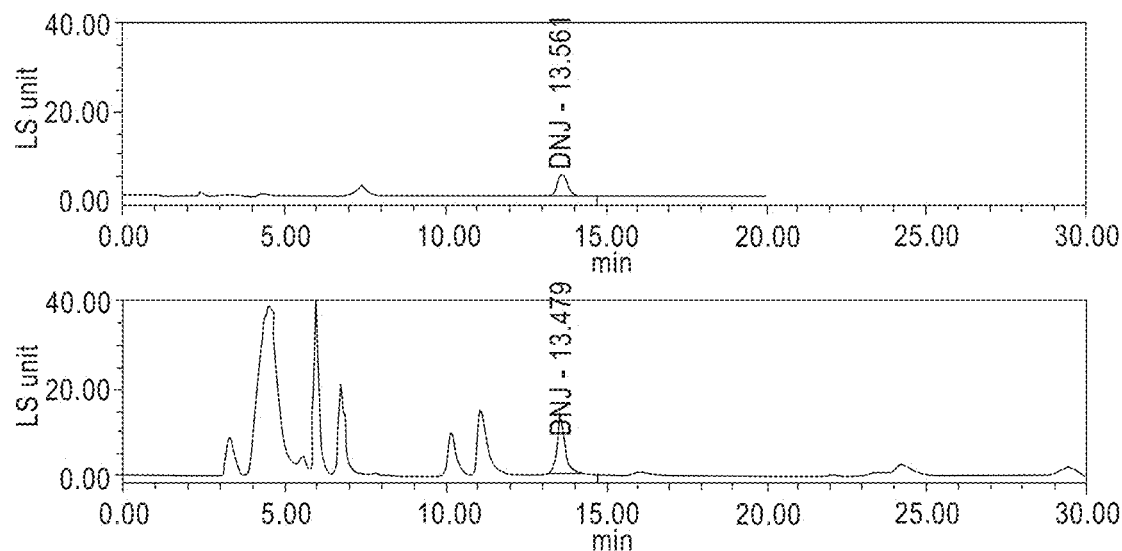
FIG. 1 is an HPLC fingerprint of the plant extract of Example 1 The upper trace is the standard HPLC of DNJ and the bottom trace the HPLC fingerprint of the plant extract of Example 1.

The imino sugar content was determined using an assay as follows and the result is shown in FIG. 1 the lower profile of which is a HPLC chromatogram showing the major imino peaks (the DNJ standard is shown in the upper profile).

(a) Weigh accurately an appropriate quantity of DNJ as a control, add methanol to make a solution of 0.1 mg/ml and shake well. Transfer 1 ml of the solution, measured accurately, to a 25 ml volumetric flask, to which add 1 ml of 0.4 mol/L boric acid-potassium chloride buffer solution (pH 8.5) and 2 ml of 5 mmol/L FMOC-CI in anhydrous acetonitrile. After ultrasonicating for 20 min. at room temperature, immediately add 2 ml of 0.2 mol/L glycine solution and 0.1% acetic acid to volume, shake well to obtain the control sample solution.

(b) Dissolve 0.3 g of the extract in an appropriate amount of water and pass through a pre-treated polyamide column. Elute with a hydrochloric acid solution (pH 3). Collect the eluent, which was then condensed under vacuum to about 10 ml. Put the solution on to a pre-treated anion exchange resin column. Wash the column with water and collect the eluent. After being condensed under vacuum to about 30 ml, the eluent was transferred to a 50 ml volumetric flask and water added to volume. Transfer 1 ml of the solution, measured accurately, to a 25 ml volumetric flask and follow the above procedure in (a) starting from "to which add 1 ml . . . " to obtain the test solution.

(c) The solutions were run on an HPLC as follows and the imino content determined therefrom (by Empower). Absorbent: C18-ODS; Mobile phase: acetonitrile: 0.1% acetic acid (30:70), running for 30 min, change the mobile phase to acetonitrile: 0.1% acetic acid (70:30) running for 10 min. Balance the system using the original mobile phase before injecting the next sample. Chromatogram recording time was 30 min with the detecting wavelength at 265 nm. Inject 20 μl, measured accurately, of the control solution and test solution, respectively, to the HPLC apparatus and run to obtain HPLC results.

The total amino acid content was assayed using a standard amino acid analysis instrument.

EXAMPLE 2

Pulverize 100 kg of dry mulberry leaves of the species Morus alba and extract under reflux 3 times (1 hour each time) with 18 folds of water (to the weight of the raw material). Pass the extract through a column filled with strong acidic cationic resin, such as Dowex-50. The volume of the column was 1/20 of the extract. Wash the column with water (2 folds of the column volume) followed by 0.5 N ammonium water (8 folds of the column volume) at a flow rate of 3 folds of the column volume per hour. Collect the ammonium water eluent with a pH of 9-11. Condense to a given volume, remove the ammonium and adjust to pH 7. Run the eluent through a column filled with a macroporous resin, such as, HP20. The volume of the column was 1/20 of the eluent and the flow rate 4 folds of the column volume per hour. The collected fluid was then dried under vacuum and the dried product pulverized to pass through a 80 mesh sieve. 1.4 kg of a pale yellow powder was obtained, which contained 4.3% DNJ, 19% total imino sugars and 40% total amino acids. The UV spectrum is illustrated in FIG. 2. The two distinct peaks differentiate the extract from other *Morus* extracts (See FIG. 3) which contain higher proportion of impurities. These impurities results in no distinction between peaks, and could lead to lower levels of efficacy.

EXAMPLE 3

Pulverize 20 kg of dry mulberry leaves of the species *Morus alba* and extract under reflux 3 times with 5 folds of 40% ethanol to the weight of the raw material. Filter the combined extract, to which an equal volume of ethanol was added, stir with constant speed for half an hour and leave it overnight. Remove the precipitate by centrifuging at 12000 r/min for 15 min, recover ethanol to a given volume. Pass the supernatant liquid through a column filled with a strong acidic cationic resin, e.g.001×7 type. The volume of the column was ⅓ of the liquid. Wash the column with water (same amount as the column volume) and elute with 1.0 N ammonia water (2 folds of the column volume) with a flow rate of the column volume per hour. Collect the ammonia water eluent with a pH 9-11. Condense to a given volume, remove ammonium and adjust to pH 7. Pass the eluent through a column filled with a macroporous resin, such as S-8. The volume of the column was 1/13 of the eluent and the flow rate, the column volume per hour. The collected fluid was then dried under vacuum and the dried product pulverized to pass through an 80 mesh sieve. 0.11 kg of a nearly white powder was obtained, which contained 9.1% DNJ, 29% total imino sugars and 32% total amino acids.

EXAMPLE 4

Pulverize 50 kg of dry mulberry leaves of the species *Morus alba* and extract under reflux 3 times with 12 folds of 40% ethanol to the weight of the raw material. Filter the combined extract and add a precipitation agent, aluminium potassium sulphate, to pH 3, and stir for 30 min. After leaving it for 2 hours, remove the precipitate by centrifuging. Adjust the supernatant to pH 7. Pass the supernatant through a column filled with a cationic resin, 001×7. The volume of the column was 1/13 of the liquid. Wash the column with water (2 folds of the column volume) and elute with 0.2 N ammonia water (8 folds of the column volume), at a flow rate of the column volume per hour. Collect the ammonium water eluent with a pH of 9-11. Condense to a given volume, remove ammonium and adjust to pH 7. Put the eluent liquid through a column filled with a macroporous resin AB-8. The volume of the column was 1/20 of the eluent and the flow rate, 2 folds of the column volume per hour. The collected fluid was then dried under vacuum, the dried product pulverized and passed through an 80 mesh sieve. 0.12 kg of a nearly white powder was obtained, which contained 18.6% DNJ, 39% total imino sugars and 21% total amino acids.

EXAMPLE 5

Pulverize 50 kg of dry mulberry leaves of the species *Morus alba* and extract under reflux 4 times with 11 folds of 25% ethanol to the weight of the raw material. Filter the combined extract, which was then put through a cationic resin column filled with Amberlite IR-120 (H+) type. The volume of the column was 1/15 of the liquid. Wash the column with water (1.5 folds of the column volume) and elute with 0.7 N ammonia water (5 folds of the column volume), at a flow rate of 1.5 folds of the column volume per hour. Collect the ammonia water eluent with a pH of 9-11. Condense to a given volume, remove the ammonium and adjust to pH 7. Put the eluent through a column filled with an S-8 macroporous resin. The volume of the column was ⅕ of the eluent and the flow rate was a column volume per hour. The collected fluid was then dried under vacuum and the dried product pulverized to pass through a 80 mesh sieve. 0.46 kg of a pale yellow powder was obtained, which contained 5.6% DNJ, 24% total imino sugars and 48% total amino acids.

EXAMPLE 6

Pulverize 5 kg of dry mulberry leaves of the species *Morus alba* var. *multicaulis* L. and extract under reflux 3 times with 11 folds of 25% ethanol to the weight of the raw material. Filter the combined extract, which was then put through a column filled with a cationic exchange resin type 001 X7. The volume of the column was 1/13 of the liquid. Elute the column with water (2 folds of the column volume) followed by 0.5 N ammonia water (5 folds of the column volume) with a flow rate of 1.5 folds of the column volume per hour. Collect the ammonia water eluent with a pH of 9-11. Condense to a given volume, remove ammonium and adjust to pH 7. Put the eluent through a column filled with a macropous resin HP20. The volume of the column was 1/10 of the eluent liquid and the flow rate 4 folds of the column volume per hour. The collected fluid was then dried under vacuum and the dried product pulverized to pass through an 80 mesh sieve. 48 g of a pale yellow powder was obtained, which contained 2.1% DNJ, 8.3% total imino sugars and 65% total amino acids.

EXAMPLE 7

Pulverize 5 kg of dry mulberry leaves of the species *Morus nigra* and extract under reflux 3 times with 8 folds of 80% ethanol to the weight of the raw material. Filter the combined extract and condense it to about 6 L, to which about 12 L of ethanol was added. Stir with a constant speed for half an hour and leave it overnight. Remove the precipitate by centrifuging at 12000 r/min for 15 min, recover the ethanol to a given volume and add an appropriate quantity of a flocculant, such as aluminium sulphate. After complete precipitation, by setting aside, remove the precipitate by centrifugation. Pass the supernatant liquid through a column filled with a cationic exchange resin, such as 001X7. The volume of the column was 1/10 of the liquid. Wash the column with water (same amount as the column volume) followed by 0.5N ammonia water (4 folds of the column volume) with a flow rate of 3 folds of the column volume per hour. Collect the ammonia water eluent with a pH of 9-11. Condense to a defined volume, remove ammonium and adjust to pH 7. Put the eluent liquid through a column filled with a macroporous resin HP20. The volume of the column was 1/15 of the eluent liquid and the flow rate, 4 folds of the column volume per hour. The collected fluid was then dried under vacuum and the dried product pulverized to pass through an 80 mesh sieve. 40 g of a nearly white powder was obtained, which contained 3.9% DNJ, 15% total imino sugars and 58% total amino acids.

EXAMPLE 8

Pulverize 5 kg of dry mulberry leaves of the species *Morus australis* Poir. and extract under reflux 3 times with 8 folds of 80% ethanol of the weight of the raw material. Filter the combined extract, which was then put through a column filled with Amberlite IR-120 (H+) type cationic resin. The volume of the column was 1/10 of the liquid. Elute the column with water (1.5 folds of the column volume) followed by 0.7 N ammonia water (5 folds of the column volume) at a flow rate of 1.5 folds of the column volume per hour. Collect the ammonia water eluent with a pH 9-11. Condense to a given volume, remove ammonium and adjust to pH 7. Put the eluent liquid through a column filled with an AB-8 macroporous resin. The volume of the column was 1/13 of the eluent liquid and the flow rate, 2 folds of the column volume per hour. The collected fluid was then dried under vacuum and the dried product pulverized to pass through an 80 mesh sieve. 42 g of a pale yellow powder was obtained which contained 1.4% DNJ, 5.2% total imino sugars and 68% total amino acids.

EXAMPLE 9

Pulverize 50 kg of dry mulberry leaves of the species *Morus alba* and extract under reflux once with 10 folds of 30% ethanol of the weight of the raw material. Filter the extract, which was then put through a column filled with Amberlite IR-120 (H+) type cationic resin. The volume of the column was 1/13 of the liquid. Elute the column with water (1.5 folds of the column volume) followed by 0.7N ammonia water (7 folds of the column volume) with a flow rate of 2 folds of the column volume per hour. Collect the ammonia water eluent with a pH of 9-11. Condense to a given volume, remove ammonium and adjust to pH 7. Put the eluent through a column filled with an AB-8 macroporous resin. The volume of the column was 1/15 of the eluent and the flow rate was the column volume per hour. The collected fluid was then dried under vacuum and the dried product pulverized to pass through an 80 mesh sieve. 0.5 kg of a pale yellow powder was obtained which contained 4.2% DNJ, 22% total imino sugars and 46% total amino acids.

EXAMPLE 10

Mix 8 portions of stearic acid, 5 portions of glycerol monostearate, 3 portions of liquid paraffin, 8 portions of spermaceti wax, 1 portion of bee wax and 5 portions of silicon oil, and heat to 75° C. (forming "Base 1"). Mix 0.7 portions of triethanolamine, 5 portions of glycerin, 0.05 portions of methylparaben and heat to 75° C. (forming "Base 2"). To the combined bases 1 and 2, add 3 portions (w/w) of the mulberry leaf extract of Example 1, mix well and add water to 100 ml. When cooled add an adequate amount of fragrance to produce a beauty whitening cream containing the said mulberry leaf extract.

EXAMPLE 11

Mix 7 portions (w/w) of glycerine, 4 portions of propylene glycol, 0.2 portions of 30% NaOH and 0.1 portions of potassium sorbate. Add distilled water to 100 ml to obtain the water phase. Separately mix 10 portions of stearic acid, 8 portions of butyl stearate, 1 portion of glycerol monostearate and 3 portions of stearyl alcohol and heat to obtain the oil phase. Heat the above water phase to 95° C. Slowly add the oil phase to the water phase at the same temperature with continuous stirring. At about 45° C., add to the mixture 2 portions of the mulberry leaf extract of Example 4 and 0.4 portions of magnesium L-ascorbyl-2-phosphate, and a few drops of fragrance, and keep stirring until the two phases are mixed. Cool to obtain a paste.

EXAMPLE 12

Mix 7 portions (w/w) of glycerine, 4 portions of propylene glycol, 0.2 portions of 30% NaOH and 0.1 portions of potassium sorbate. Add distilled water to 100 ml to obtain the water phase. Separately mix 10 portions of stearic acid, 8 portions of butyl stearate, 1 portions of glycerol monostearate and 3 portions of stearyl alcohol and heat to obtain the oil phase. Heat the above water phase to 95° C. Slowly add the oil phase to the water phase at the same temperature with continuous stirring. At about 60° C., add to the mixture 2 portions of the mulberry leaf extract of Example 1 and 0.2 portion of DEP-11. Add a few drops of fragrance and keep stirring until the two phases were mixed well. Cool to obtain a paste.

EXAMPLE 13

To 0.4 portions (w/w) of the mulberry leaves extract of Example 5 add 0.1 portions of ethylparaben, 0.5 portions of sodium bisulphate, 0.1 portions of disodium edentate and 9 portions of glycerine, and add distilled water to 100 ml to obtain the lotion.

EXAMPLE 14

Mix well 5 kg of the mulberry leaf extract of Example 1 with 1.8 kg of starch, 1.5 kg of microcrystalline cellulose, 0.45 kg of cross-linked PVP, 0.55 kg of CSM-Na, and appropriate quantities of magnesium stearate and silicon micro-powder. Make 20,000 tablets, weighing about 0.5 g each.

EXAMPLE 15

Mix 1.0 kg of the mulberry leaf extract in Example 3 with an appropriate quantity of starch, fill in 10,000 capsules to make each capsule contain 100 mg of the extract.

EXAMPLE 16

To 2.0 kg of the mulberry leaf extract of Example 3 add 0.5 kg of vitamin C, 1.0 kg of citric acid, 0.8 kg of sodium bicarbonate, 0.08 kg of mannitol, PVP, PEG 6000, flavouring agent and bonding agent to make effervescent granules.

Activity Test Experiments

Experiment 1. Inhibition Activity Assay of the Mulberry Leaf Extract on α-glucosidase The aim was to investigate the inhibition activity of the mulberry leaves extract in the present disclosure on α-glucosidase. The reagents and apparatus are set out below:

(1) Mulberry leaves extract of Example 1, (2) DNJ standard reference chemical, (3) α-glucosidase (Type I from Bakers yeast, EC232.604.7), made into a 0.42 U/ml solution using 0.1 mol/L phosphoric acid buffer (pH 6.8)

(4) pNPG, made into a 5 mmol/L solution using 0.1 mol/L phosphoric acid buffer (5) pNP, made into a 200 µmol/L solution using 0.1 mol/L phosphoric acid buffer (pH 6.8)
(6) Multi skan Ascent microplate reader (Thermo Electron Co., USA)

The method was as set out below:

Standard Curve

Dilute the 200 µmol/L pNP solution using 0.1 mol/L phosphoric acid buffer, respectively, to 100 µmol/L, 50 µmol/L, 25 µmol/L, 12.5 µmol/L, 6.25 µmol/L and 3.125 µmol/Ln. From each of the diluted solutions take 200 µl for OD measurements at 405 nm and use the OD values to draw the standard curve.

Test Sample Assay (1) Put 80 µl each of the test sample of different concentrations into individual wells of the microplate and 80 µl phosphoric acid buffer solution as placebo.
(2) To each well, add 30 µl enzyme (0.42 U/ml), place on the bench for 30 s, incubate together with the substrate (pNPG) for 15 min. at 37° C. and turn on the microplate reader, set the temperature at 37° C., measurement mode to kinetic and interval at 10 s. Take the readings 13 times (total 2 min.).
(3) To each well add 90 µl substrate (5 mmol/L pNPG) shake on the bench for 30 s, place into the microplate reader, press START, continuously measure the OD values at 37° C.
(4) With the concentrations of pNP as X axis and OD values as Y axis, draw the standard curve. Use the OD values obtained in step (3) against the standard curve to get related quantities of the reaction product.
(5) For the placebo and the test samples of different concentrations, take the time as X axis and product quantity as Y axis to draw a reaction progress curve. The slope of the straight line is the reaction speed.
(6) With the concentration of the test samples as X axis and reaction speed as Y axis, establish the test sample concentration curve and obtain $IC_{50}$. Inhibition activity (U/µg)=(0.5×enzyme activity of each well)/($IC_{50}$×the volume of the samples of each well)=(0.5×0.42×0.03)/($IC_{50}$×0.08)=0.07875/$IC_{50}$.

Figure 5A:
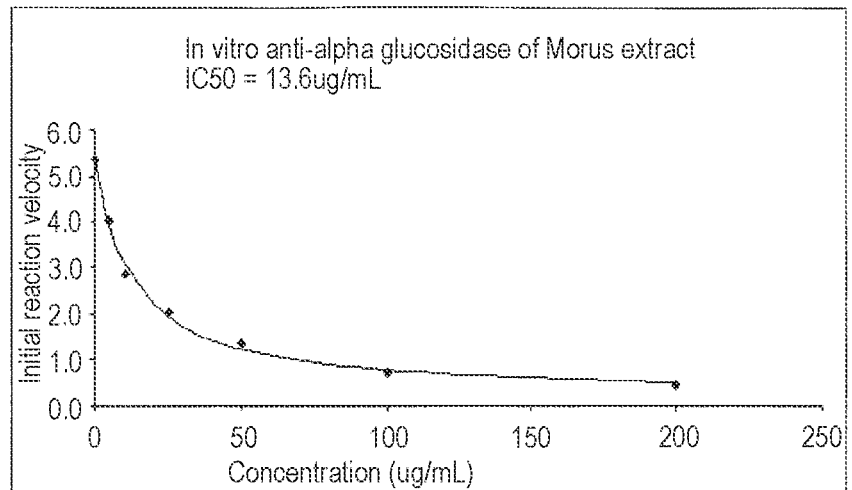
FIGS. 5a and b show the level of α-glucosidase inhibition by Morus extract (5a) and DNJ (5b)
Figure 5B:
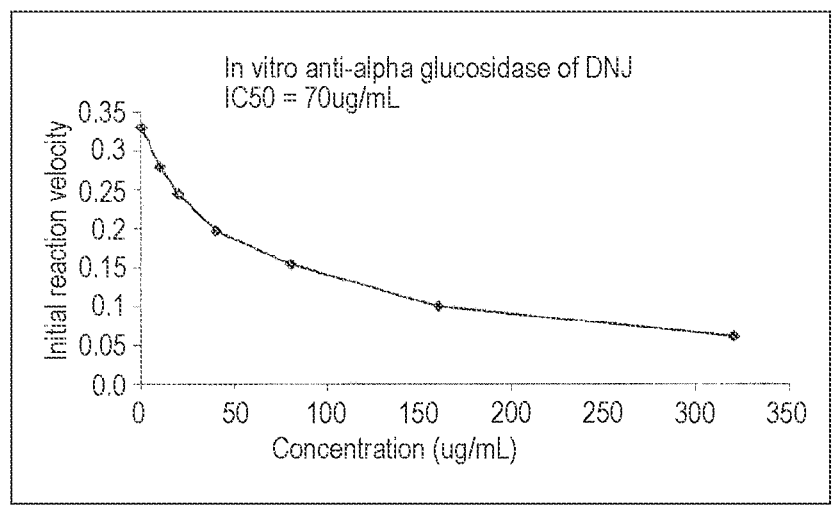

Results and Discussion:

The results of the above experiment showed that the $IC_{50}$ of the mulberry leaves extract in Example 1 had an ICso value of 13.6 µg/ml in inhibiting α-glucosidase whilst that of pure DNJ was 70 µg/ml. This demonstrated that the activity of the former was much greater than the latter. Considering the fact that the DNJ content in the mulberry leaves extract in Example 1 was only 3.5%, it becomes possible to use the said extract to achieve the same or better activity whilst reducing the likely adverse reactions caused by the use of higher concentrations of the pure compound. See FIGS. 5a and b, which show respectively the in vitro inhibition of ogucosidase by *Morus* extract and DNJ, Initial reaction velocity versus concentration.

Experiment 2: Inhibition Activity Assay of the Mulberry Leaf Extract and Arbutin on TYR The aim was to investigate the impact and mechanisms of action of the test samples on the TYR activity in melanoma cell line B16. The reagents and apparatus were as set out below::

(1) Mulberry leaf extract of Example 1
(2) DNJ standard reference chemical
(3) Arbutin standard reference chemical
(4) L-dopa solution 1 mg/ml in pH 6.8 phosphoric acid buffer, prepared immediately before use
(5) WIP cell lysis buffer
(6) Cell culture place (24 wells and 96 wells)
(7) Optical microscopy
(8) Centrifuge
(9) Microplate reader The methods were set out as below B16 melanoma cells were washed with phosphate-buffered saline and collected in a centrifuge tube. After centrifugation, WIP-lysis buffer containing phenyl- methylsulfonyl fluoride (PMSF) was added to the cell pellet to lyse the cells and the solution was left to stand on ice for 30 minutes. The solution was subsequently centrifuged for 10 min, at 12000 g, at 4° C., with the supernatant (cell extract) containing the cellular components being retained for assay purposes.

To determine the direct effect of DNJ, arbutin, and *Morus* extract on tyrosinase catalytic activity, 60 µl DNJ, arbutin or *Morus* extract (concentration of compounds used varied) were added to 60 µl cell extract in a 96-well microplate. The plate was incubated at 37° C. for 1 hour, and then 80 µl L-dopa was added to each well. The absorbance (492 nm) of each well was recorded at 5 minute intervals for 30 minutes at 37° C. using a microplate reader.

Results and Discussion

Figure 6:
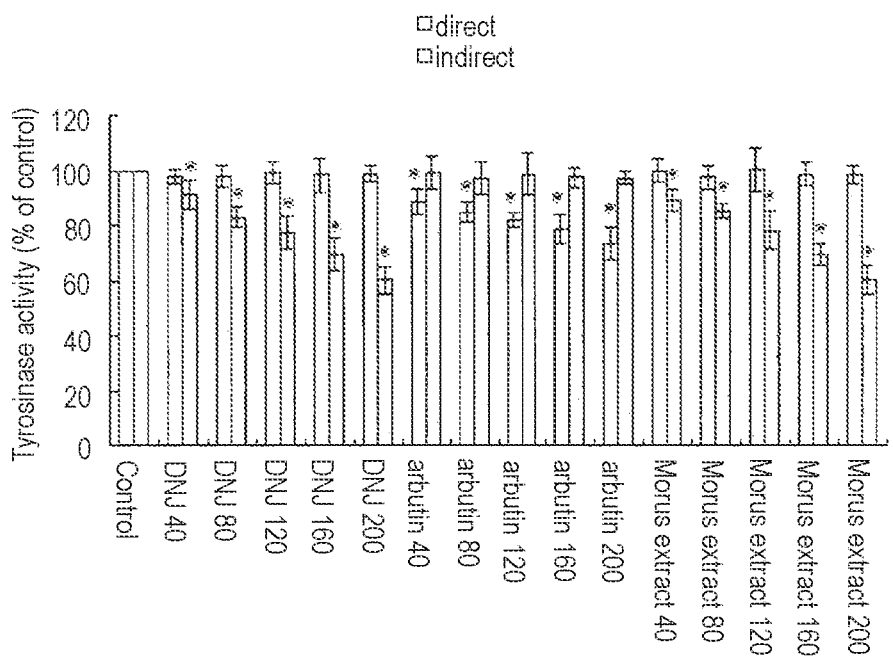
FIG. 6 is the comparative effect of DNJ, arbutin and Morus extract on tyrosinase.

The results of the assays can be seen in FIG. 6. The light columns show the direct effect of DNJ, arbutin, and *Morus* extract on tyrosinase activity in the cell extracts, whilst the dark columns show the results of the indirect effects of the compounds of tyrosinase activity.

In the direct activity assay, arbutin reduced the activity of tyrosinase in a dose-dependent manner, whilst DNJ and *Morus* extract showed no effect on tyrosinase activity. However, in the indirect activity assay, after the cells had been incubated for three days incubation in the presence of the test compounds, there was a dose-dependent decrease in tyrosinase activity in the DNJ and *Morus* extract groups, but cells incubated with arbutin showed no effect on tyrosinase activity.

These findings are in-line with the reported literature and support the proposed different mechanism of action for the α-glucosidase inhibitors, DNJ and *Morus* extract. In the direct activity assay, arbutin directly interacted with tyrosinase, binding to the active site and inactivating the enzyme, therefore reducing the oxidation of L-dopa to o-dopaquinone, α-Glucosidase inhibitors do not directly affect the activity of tyrosinase and this was reflected in the results of the direct activity assay where DNJ and *Morus* extract were shown to have no tyrosinase inhibitory activity.

In the indirect activity assay, both DNJ and *Morus* extract were shown to have inhibitory activity over tyrosinase. α-Glucosidase inhibitors act on immature tyrosinase, and by preventing the binding of calnexin during tyrosinase maturation, there are conformational changes that affect the enzymatic activity of the mature tyrosinase. These changes were evidenced by the decrease in enzymatic activity after three days incubation with DNJ and *Morus* extract. Arbutin directly competes for the tyrosinase active site and in the indirect assay, where arbutin was not present in the assay solution, there was no inhibition of enzymatic activity.

Experiment 3. Impact on the Melanin Content in Melanocytes by the Mulberry Leaf Extract of the Disclosure The aim was to investigate the impact of the test samples on melanin content of melanoma cell line B16. The reagent and apparatus used are set out below:

(1) Mulberry leaf extract of Example 1
(2) DNJ standard reference chemical
(3) VC PMGstandard reference chemical
(4) WIP lysis buffer
(5) Optical microscope
(6) Cell culture plate (24 wells and 96 wells)

(7) Centrifuge (8) Microplate reader

The method was as set out below:

1. Harvest the melanoma B16 cells at Log phase and adjust the cell suspension to an appropriate concentration, divide into 24 well plates and allow the cells to adhere to the walls.
2. To each well add 1 ml test sample of different concentration made by diluting with the medium (4 duplicates for each concentration). Incubate for 2 days, refresh the sample solution and continue to incubate for 2 days.
3. Harvest the cells on day 4 and wash thoroughly twice with PBS. Add 250 µl WIP lysis buffer and allow to lyse in an ice bath, vortex mixing once every 5 min for 4-5 times.
4. Centrifuge for 10 min at 12000 rpm at 4° C. Discard the supernatant and dissolve the precipitate with 400 µl 1N NaOH and keep it in a 80° C. water bath for 1 hour.
5. Use a microplate reader to measure OD value at 405 nm, and calculate the relative content.

Figure 7:
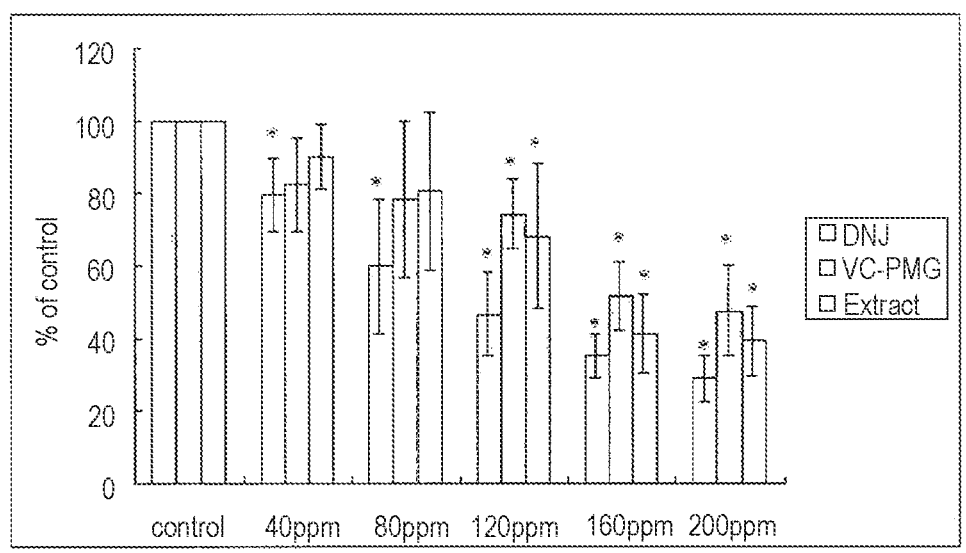
FIG. 7 is the comparative effect of DNJ, VC-PMG and Morus extract on melanin synthesis inhibition.

Results and Discussion:

The results of the assays can be seen in FIG. 7 The midtone columns showed the inhibitory effect of DNJ on melanin content in B16 melanoma cells, whilst the dark columns and light columns showed the results of the inhibitory effects of VC-PMG and *Morus* extract on melanin content in B16 melanoma cells. All effects are after 3 days incubation with DNJ, VC-PMG or *Morus* extract at different concentration.

Compared to the control the content of melanin in the treatments of DNJ, VC-PMG and Example 1 at different concentration levels decreased significantly in a dose-dependent manner. The activity intensity of the three compounds, from strong to weak, was: DNJ>*Morus* extract>VC-PMG.

DNJ is an active compound identified from *Morus* extract, as an α-glucosidase inhibitor andean reduce the activity of tyrosinase resulting in reduction of melanin in B-16 melanoma cell lines. Since the content of natural occurring DNJ in all plants is very low, it is impossible to use natural DNJ for a commercial purpose. But with *Morus* extract, although the DNJ content in *Morus* extract is as low as 2-5%, *Morus* extract still demonstrated a similar potency of activity to DNJ, which indicated that within *Morus* xtract, DNJ may work synergistically with other active compounds to generate a strong anti-pigmentation effect.

From our observation, when the concentration of VC-PMG applied to the B16 melanoma cell increased to over 200 ppm, the viability of the cell decreased, which indicated that an excessive concentration of VC-PMG may cause harm to the cells. *Morus* extract, as a natural product, has a better safety profile and a stronger efficacy compared to VC-PMG, and its mechanism of action differ from VC-PMG, thus *Morus* extract can be either used alone or combined with VC-PMG to achieve a better anti-pigmentation effect.

In order to develop *Morus* extract as the lightening products in cosmetics, we considered the dosage of lightening ingredient usually used in cosmetics: arbutin: 1%-5%, kojic acid: 0.2%-3%, vitamin derivates: <3%. Based on our study, the recommend dosage of Example 1 is below 3%.

Experiment 4. Impact of the Mulberry Leaf Extract of the Present Disclosure on the Growth of Melanocytes Methods Cell Viability Cell survival was measured using the MTT assay, which is based on the conversion of 3-(4,5-dimethylthiazol-2-yl)-2,5-diphenyltetrazolium bromide to MTT-formazan crystal by mitochondrial enzyme in viable cells. MTT was freshly prepared at 2 mg/ml in phosphate-buffered saline (PBS). $2 \times 10^4$ cells per ml were plated in 96-well plates, DNJ, VC-PMG, *Morus* extract or DMEM were added to the culture medium. Aliquots of 20 µl of MTT stock solution were added to the well at different time points throughout the experiment, and the plate was incubated at 37° C. for 4 h in a humidified 5% $CO_2$ incubator. After 4 h, the formazan crystals of these cells were solubilized in 1000 DMSO by gentle shaking. After 10 min, the amount of formazan was quantified spectrophotometrically using an ELISA plate reader at 540 nm.

Determination of Melanin Content in Melanoma Cells

The B16 melanoma cells were seeded at a density of $4 \times 104$ cell per well of 24-well culture plates, incubated at 37° C. under 5% $CO_2$ atmosphere for 24 h. The cells were then treated with various concentrations of DNJ, VC-PMG or *Morus* extract for 3 days. The cells were washed with phosphate-buffered saline, collected in centrifuge tube. After centrifugation, cell pellets were disrupted in WIP lysis buffer containing phenylmethylsulfonyl fluoride (PMSF) on ice for 30 min. The solution was centrifuged for 10 min at 12000 g at 4° C., the pellets were dissolved in 1 N NaOH by boiling for 1 h at 70° C. The melanin content was assayed at 405 nm in a spectrophotometer.

Results and Discussion

The effects of DNJ, VC-PMG and *Morus* extract on Cell viability

Figure 8A:
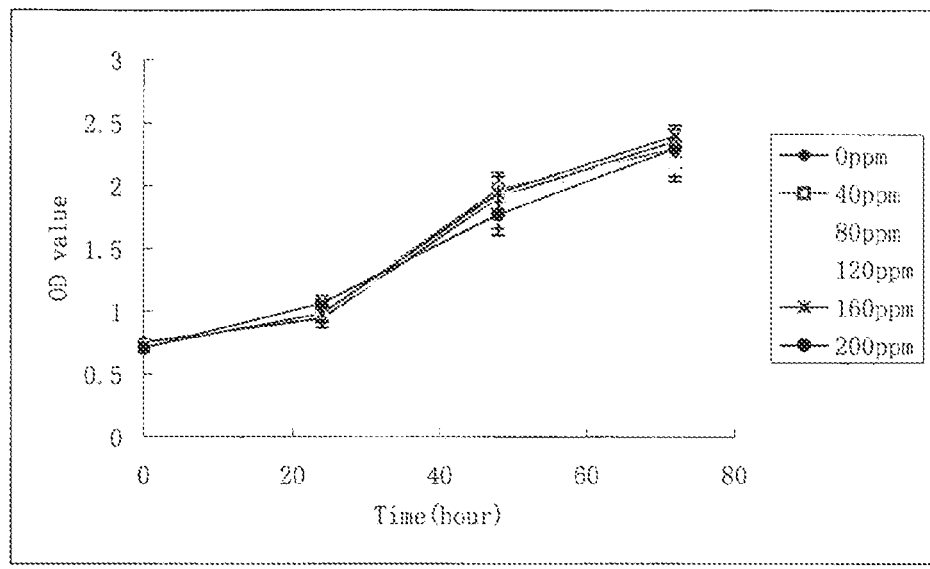
FIGS. 8a, b and c show comparative cell toxicity of DNJ (a), VC-PMG (b) and Morus extract (c)
Figure 8B:
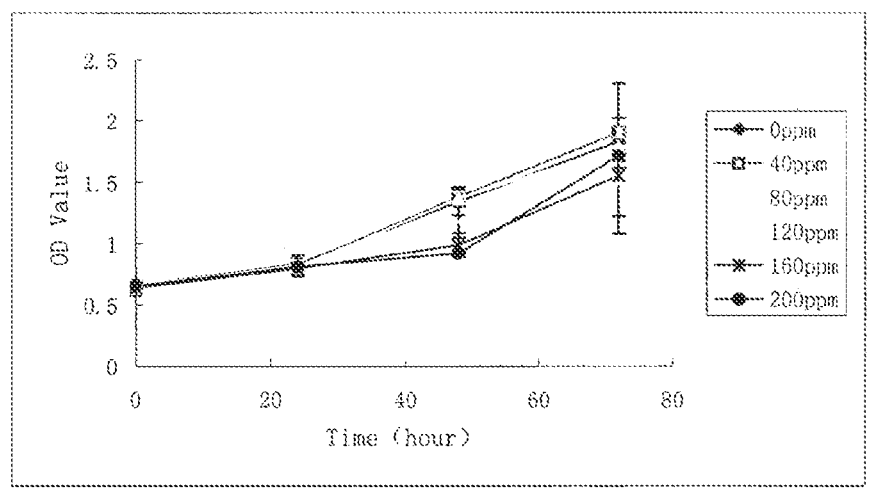
Figure 8C:
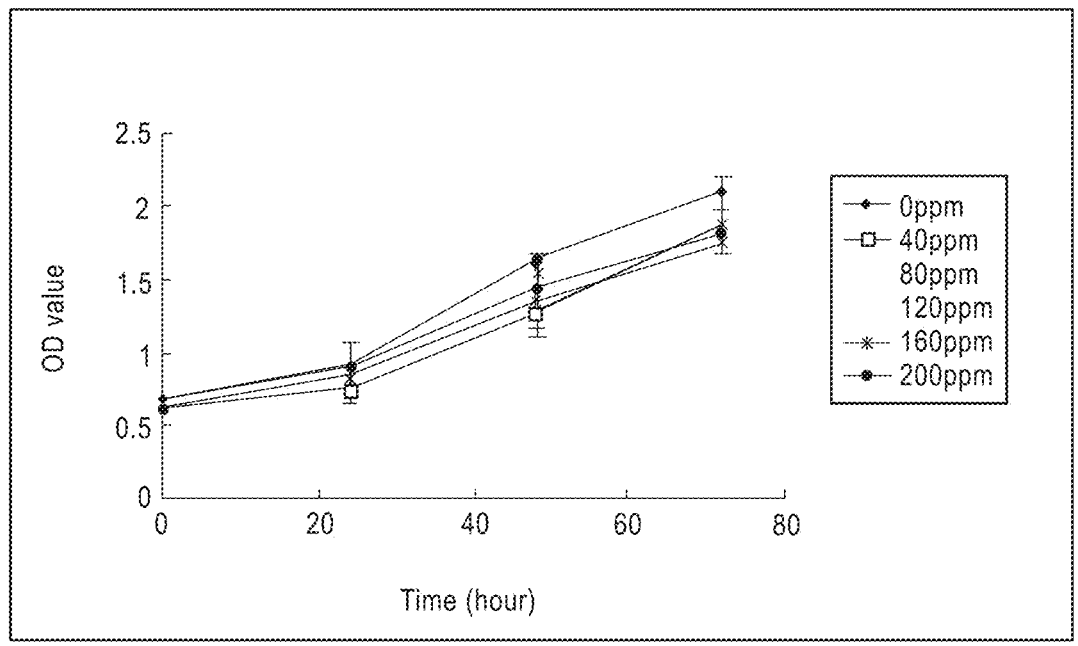

The data on the cell viability assay using MTT for B16 melanoma cells were given in FIG. 8A, FIG. 8B and FIG. 8C.

DNJ, VC-PMG and *Morus* extract induced no growth inhibition of B16 melanoma cells at the given concentration. These data clearly showed the non-cytotoxic nature of DNJ, VC-PMG and *Morus* extract in B16 melanoma cell below the concentration of 200 ppm, and indicate that cell growth was not an influence for the assay of melanin content below.

Experiment 5: Impact of the Mulberry Leaf Extract of the Disclosure on the Blood Glucose of Wistar Rats The reagents and apparatus are set out below:

(1) Mulberry leaf extract of Example 1

(2) Saline (3) Miglitol standard reference chemical (4) 64 Wistar rats (5) Johnson's One Touch Ultra blood glucose meter and Code 9 blood glucose test strips Animals received *Morus* extract via intraperitoneal injection (15 mg/kg or 30 mg/kg) or intragastrically (25 mg/kg or 50 mg/kg). Miglitol (Glyset®) (25 mg/kg), an α-glucosidase inhibitor approved for type-2 diabetes was used as a positive control. Fasted blood-sugar levels were recorded as a baseline, and blood sugar levels were measured at time intervals 05.hr, 1 hr and 2 hrs after receiving a starch meal. The animals were dosed with *Morus* extract prior to receiving the starch meal.

Results and Discussion:

Blood glucose in 0.5 h, 1 h, 2 h after giving starch (X ± SD, n = 10)

| Groups | Dose (mg/kg) | Fasted Glucose (mmol/L) | 0.5 h (mmol/L) | 1 h (mmol/L) | 2 h (mmol/L) |
|---|---|---|---|---|---|
| Normal control | / | 3.07 ± 0.79 | 3.06 ± 0.77 | 3.51 ± 0.76 | 3.22 ± 0.47 |
| ig | 25 mg/kg | 3.02 ± 0.71 | 2.38 ± 0.49* | 3.20 ± 0.56 | 3.05 ± 0.59 |
| ig | 50 mg/kg | 3.02 ± 0.73 | 2.23 ± 0.40** | 2.89 ± 0.59 | 2.7 ± 0.59* |
| ip | 15 mg/kg | 3.05 ± 0.80 | 2.61 ± 0.54 | 3.29 ± 0.39 | 3.15 ± 0.50 |
| ip | 30 mg/kg | 3.06 ± 0.78 | 2.34 ± 0.41* | 3.43 ± 0.54 | 2.97 ± 0.41 |
| Positive Control^ | 25 mg/kg | 3.04 ± 0.74 | 2.27 ± 0.71** | 2.98 ± 0.52 | 2.69 ± 0.35* |

Figure 9:
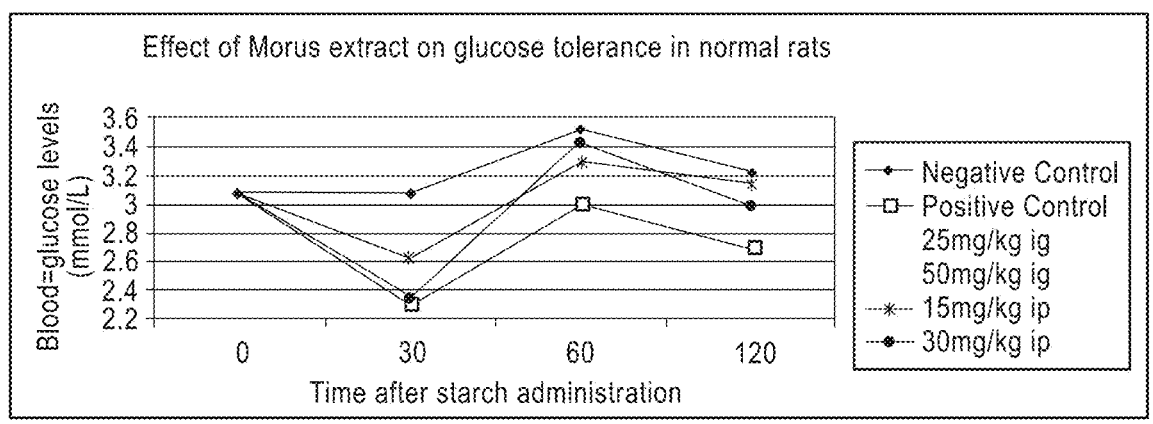
FIG. 9 is the glucose lowering effect of Morus extract in Wistar rats.

The results of showed that *Morus* extract significantly reduced blood-glucose levels. The intragastric route of administration showed that the active compounds have good oral bioavailability and are not inactivated through metabolism. The both intragastic and intraperitoneal doses significantly lowered blood glucose levels with the 50 mg/kg dose being as effective as miglitol (Glyset®) in this study. See FIG. 9

Experiment 6: Effect of Mulberry Extract on Reducing Blood Glucose Levels in Humans Method In a small human study, participants received either 400 mg *Morus* extract or placebo, plus 50 g soft sugar after an overnight fast. Blood sugar levels were monitored for three hours. Additionally, one patient received 50 g miglitol to act as a positive control.

Results and Discussion

Figure 10:
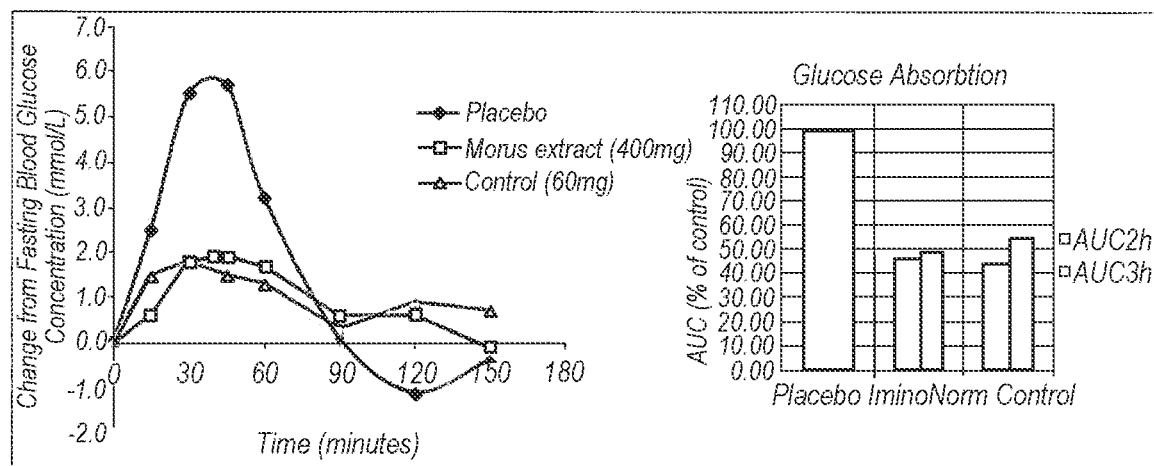
FIG. 10 is the glucose lowering effects of Morus extract in humans.

The data showed that *Morus* extract dramatically reduced blood sugar levels, reducing the initial blood sugar spike by 59.91%, reducing the blood sugar levels over two hours by 50.78%, and over three hours by 47.18%. *Morus* extract was able to reduce the glycaemic index of the soft sugar from 83.8 to 41.2. See FIG. 10

Experiment 7: Effect of Mulberry Extract on Skin Lightening in Humans

Methods

Mulberry extract as in Example 1 was made into 0.2% and 0.5% cream formulation for the study. Twenty female subjects (age 18 and older) having given informed consent, applied each formulation to predefined areas on each forearm twice daily. Prior to first treatment, measurements of skin colour where measured using a Chromameter CR300 on the defined zones.

After 28 days of treatment, subjects returned to the testing laboratory where new measurements of skin colour were made on the same defined zones as day 0.

Evaluations were made on three study parameters which were:

L* (from dark to light). This is lightness parameter of the skin. An increase in this parameter characterizes a lightening of the skin.

b* (from the blue to yellow). A decrease in this parameter characterizes a decrease in the yellow constituent of the skin.

ITA° (Individual Typological Angle). This parameter shows the skin pigmentation degree of a subject using the lightness (L*) and cutaneous melanin parameters (b*). An increase in the ITA° characterizes a decrease in skin pigmentation.

Results and Discussion

Figure 11A:
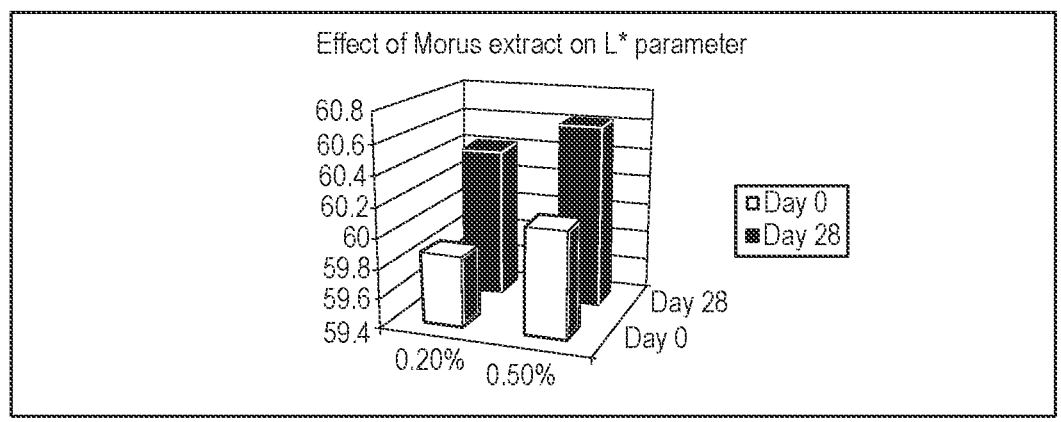
FIGS. 11a and b are the skin lightening effects of Morus extract in humans
Figure 11B:
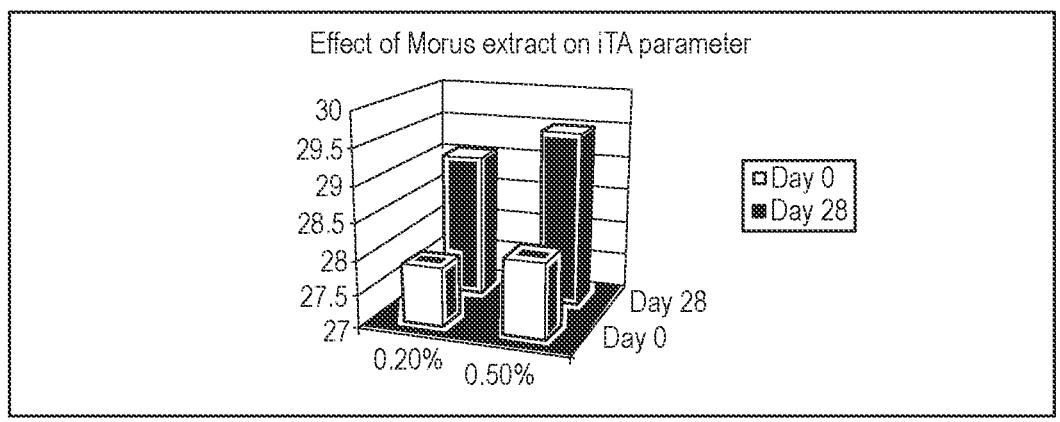

L* parameter increased significantly (P<0.001) after 28 days of daily use of the 0.2% product (+0.54 A.U. on average) representing an increased lightness in the skin colouration. This effect was observed in 90% of the subjects. See FIG. 11A The individual typological angle (ITA°) parameter increased significantly (P<0.001) after 28 days of daily use of the 0.2% product (+1 A.U. on average) indicating a decrease in skin pigmentation. This effect was observed in 57% of the subjects. See FIG. 11B For the 0.5% product: L* parameter increased significantly (P<0.001) after 28 days of daily use indicating an increase in skin lightness. This effect was observed in 86% of the subjects. See FIG. 11A The individual typological angle (ITA°) parameter for the 0.5% formulation increased significantly (P<0.001) after 28 days of daily use of product indicating a decrease in skin pigmentation. This effect was observed in 67% of the subjects. See FIG. 11B.

Experiment 8. Extract Data

The extracts of the present disclosure (Samples 1 to 3) differ from prior art extracts in their characteristics as illustrated in Table 1 below:

TABLE 1

| Sample | IC $_{50}$ (µg/ml) on α-glucosiclase I | Imino sugar content | Colour | Water solubility |
|---|---|---|---|---|
| 1 | 34 | 12% | Pale yellow | Easily |
| 2 | 42 | 19% | Pale yellow | Easily |
| 3 | 21 | 29% | Nearly white | Easily |
| 4 | 240 | 2% | Yellowish brown | Average |
| 5 | 180 | 5% | Yellow | Soluble |
| 6 | 204 | 3% | Brownish green | Average |
| 7 | 110 | 12% | Brownish green | Soluble |
| 8 | 150 | 6% | Brownish yellow | Average |

Explanation to Table 1 above:

Samples 1-3 refer to the products made in Examples 1-3;

Sample 4 refers to the product made according to Patent 03139028.5;

Sample 5 was made with the method described below: Pulverize mulberry leaves and extract under reflux with 80% ethanol for 3 times, 1-2 hours each time. For the first time, use 6 folds (w/w) of ethanol of the weight of the raw material, followed by 4 folds for both $2^{nd}$ and $3^{rd}$ times. Combine the extracts and leave it for 24 hours before filtration. Concentrate the filtrate solution and extract the condensed extract with water 5 times at 70-80° C. Each time use 10 folds of water of the weight of the starting material (mulberry leaves). Adjust the pH of the combined water extract to pH 3-4 and add NaCl to 3-5% concentration. The liquid was subjected to D101 macroporous resin chromatography with a column of 60 cm (H)×3 cm (D). Wash with water till the eluent became clear and then elute with 5 folds of 30-50% ethanol of the column volume, flow rate 20/ml. Collect the eluent, condense and dry it to obtain the sample (5).

Sample 6 was made with the method described below: Pulverize mulberry leaves and extract twice with 50-60% ethanol at 50° C., using 10-12 folds of ethanol of the weight of the mulberry leaves each time. Concentrate the extract and pass it through a column filled with D72 strong acidic macroporous resin and collect the fluid (fraction 1). Elute with ethanol to obtain fraction 2 followed by 70% ethanol containing 2% ammonium to obtain fraction 3. Centrifuge and concentrate fractions 1, 2 and 3, respectively. Dry and mix to obtain the sample (6).

Sample 7 was made with the method described below: Pulverize mulberry leaves and extract with 80° C. water twice, (10-15 folds of water). Adjust the pH of the combined extract to pH 2-3, cool it to 0° C. until complete precipitation. Filter and subject the concentrated filtrate to cationic resin chromatography. Elute with water and follow by a mixture of equal amount of 50% ethanol and ammonia water solution until the eluent became colourless. Concentrate the eluent and dry it to obtain the sample (7).

Sample 8 was made with the method described below: Pulverize mulberry leaves and extract with 30% ethanol for 3 times (5 folds of the weight of the mulberry leaves, each time). Concentrate the combined extract and to the concentrate add ethanol to precipitate. Add water to the concentrated supernatant and put it through a D101 macroporous resin column and collect the fluid. Elute with 3 folds of water and combine the fluid and water eluent to obtain fraction 1. Continue to elute the column with 60% ethanol (5 folds) to obtain fraction 2. Adjust the fraction 1 to pH4 and put it through a cation exchange column. Wash the column with water until the eluent became colourless, Elute with 0.5 N ammonia solution (8 folds) and collect the eluent to obtain fraction 3. Concentrate and dry fractions 2 and 3, respectively to obtain the sample (8).

The solubility terms used in the Table are defined below:

"Easily soluble" 1 g sample will dissolve in less than 1 ml water;

"Soluble" 1 g sample will dissolve in 10-30 ml water;

"Average" 1 g sample will dissolve in 30-100 ml water;

The above results demonstrated that the product of the present disclosure is better than the current products in activity, content of the key active principle, colour and water solubility.

The invention claimed is:

1. A plant extract obtained from *Morus* plant leaves which has an $IC_{50}$ value of less than 90 µg/ml with respect to inhibition of α-glucosidase I, comprising:
   (i) 5-40% (w/w) total imino sugars, as measured by at least one of quantitative High Performance Liquid Chromatography (HPLC) and liquid chromatography/mass spectrometry (LC-MS), the imino sugars including at least one of 1-deoxynojirimycin (DNJ), fagomine, and N-methyl-DNJ; and
   (ii) 20-70% (w/w) total amino acids;
   wherein the extract is easily soluble in water.

2. The plant extract as claimed in claim 1, wherein the $IC_{50}$ value is 5-40 µg/ml with respect to inhibition of α-glucosidase I.

3. The plant extract as claimed in claim 1, wherein the total imino sugars is 8-30% (w/w).

4. The plant extract as claimed in claim 1, wherein the total imino sugar is 15-20% (w/w).

5. The plant extract as claimed in claim 1, wherein the imino sugars further include at least one of 1,4 dideoxy-1, 4-imino-D-arabinitol (DAB), 2-O-α-D-galactopyranosyl-DNJ (GAL-DNJ) and calystegin B.

6. The plant extract as claimed in claim 1, wherein the total amino acids range from 30-60% (w/w).

7. The plant extract as claimed in claim 6, wherein the total amino acids is 40-50% (w/w).

8. The plant extract as claimed in claim 1, wherein the *Morus* is selected from

| | |
|---|---|
| a. | *Morus alba* L., |
| b. | *Morus alba* var *multicaulis* L., |
| c. | *Morus nigra*, and |
| d. | *Morus australis* Poir. |

9. The plant extract as claimed in claim 1, wherein said extract contains 1-20% (w/w) of calculated on the basis of the total weight of the extract.

10. The plant extract as claimed in claim 1, wherein the DNJ is included at a concentration of 2-10% (w/w) calculated on the basis of the total weight of the extract.

11. The plant extract as claimed in claim 1, wherein the DNJ is included at a concentration of 4-6% (w/w) calculated on the basis of the total weight of the extract.

12. The plant extract as claimed in claim 1, wherein wherein the DNJ is included at a concentration of 1-3% (w/w) calculated on the basis of the total weight of the extract.

13. The plant extract as claimed in claim 1, further comprising a pH value between 5.5-6.5 in a 1% water solution.

14. The plant extract as claimed in claim 1, wherein a UV spectrum of the extract shows a maximum absorption at 218 nm and 263 nm.

15. The plant extract as claimed in claim 1, wherein the amino acids include at least one of arginine, leucine, lysine, and phenylalanine.

16. A pharmaceutical, nutraceutical, or a food or drink additive or supplement comprising a plant extract as claimed in claim 1.

17. A food or drink comprising a plant extract as claimed in claim 1.

18. A method for producing a plant extract as claimed in claim 1, comprising the steps of:
   a. conducting a water or alcoholic extraction step from leaf material;
   b. conducting a column chromatography purification step using a strong acidic cation exchange resin, washing with water, eluting with an ammonia solution, collecting the eluent, and removing the ammonia therefrom; and
   c. concentrating and drying the extract.

19. The method as claimed in claim 18, wherein:
   a. prior to conducting the water or alcoholic extraction step, further comprising the step of drying the plant leaves into coarse powder, and wherein the extraction step is conducted with 5-18 folds of 0-40% of a low molecular weight alcohol per the quantity of the *Morus* plant leaves (w/w), and repeated up to 5 times,
   b. the step of conducting the column chromatography purification step includes washing the column with 1-2 folds of water of the column volume and discarding the wash, eluting the column with 2-8 folds of 0.2-1.0N ammonia water solution of the column volume, at an elution rate of 1-3 folds of the volume of the column per hour, and collecting the eluent with a pH value of between 9.0 and 11.0, and
   c. the step of concentrating and drying the extract includes pulverizing the dried extract to pass through a mesh sieve.

20. The method as claimed in claim 18, wherein following the step of conducting the column chromatography purification step, further comprising the step of subjecting the eluent to column chromatography using a macroporous absorption resin and collecting the solution, wherein the column is eluted with a volume ratio between the solution and the column of between 20:1 to 5:1.

* * * * *

UNITED STATES PATENT AND TRADEMARK OFFICE
CERTIFICATE OF CORRECTION

PATENT NO. : 11,865,155 B2
APPLICATION NO. : 17/367308
DATED : January 9, 2024
INVENTOR(S) : Chen Xie et al.

It is certified that error appears in the above-identified patent and that said Letters Patent is hereby corrected as shown below:

In the Claims

At Column 24, Claim number 9, Line number 13, add DNJ after the word of and before the word calculated.

Signed and Sealed this
Twenty-seventh Day of February, 2024

Katherine Kelly Vidal
Director of the United States Patent and Trademark Office